(12) United States Patent
Ditch et al.

(10) Patent No.: US 7,181,952 B2
(45) Date of Patent: Feb. 27, 2007

(54) CHARACTERIZATION OF MIST SPRAYS USING A PHASE-DOPPLER PARTICLE ANALYZER AND AN ISO-KINETIC SAMPLING PROBE

(75) Inventors: Benjamin Ditch, Boston, MA (US); Hong-Zeng Yu, Foxboro, MA (US)

(73) Assignee: FM Global Technologies, LLC, Johnston, RI (US)

( * ) Notice: Subject to any disclaimer, the term of this patent is extended or adjusted under 35 U.S.C. 154(b) by 0 days.

(21) Appl. No.: 10/868,953

(22) Filed: Jun. 17, 2004

(65) Prior Publication Data

US 2005/0126259 A1    Jun. 16, 2005

Related U.S. Application Data

(60) Provisional application No. 60/528,483, filed on Dec. 11, 2003.

(51) Int. Cl.
*G01F 1/74* (2006.01)

(52) U.S. Cl. .................... 73/29.01; 73/861.04
(58) Field of Classification Search ............. 73/53.01, 73/61.41
See application file for complete search history.

(56) References Cited

U.S. PATENT DOCUMENTS

| | | | |
|---|---|---|---|
| 4,540,283 A | 9/1985 | Bachalo | |
| 4,545,260 A | 10/1985 | Benton et al. | |
| 4,566,342 A * | 1/1986 | Kurz ..................... | 73/863.03 |
| 4,633,714 A | 1/1987 | Mazumder et al. | |
| 4,662,749 A | 5/1987 | Hatton et al. | |
| 4,701,051 A | 10/1987 | Buchhave et al. | |
| 4,754,651 A | 7/1988 | Shortridge et al. | |
| 4,767,315 A * | 8/1988 | Brannstrom et al. ........... | 431/7 |
| 4,854,705 A | 8/1989 | Bachalo | |
| 4,919,536 A | 4/1990 | Komine | |
| 4,986,659 A | 1/1991 | Bachalo | |
| 5,315,306 A | 5/1994 | Doughty et al. | |
| 5,686,989 A * | 11/1997 | Hoffman et al. ............ | 356/336 |
| 5,693,894 A | 12/1997 | Jobson | |
| 5,889,201 A * | 3/1999 | Turchin et al. ............ | 73/53.01 |
| 6,016,751 A | 1/2000 | Hess | |
| 6,085,585 A | 7/2000 | Yu et al. | |
| 6,499,357 B2 | 12/2002 | Alpert et al. | |
| 6,672,374 B1 * | 1/2004 | Lin ............................ | 165/121 |

\* cited by examiner

*Primary Examiner*—Hezron Williams
*Assistant Examiner*—Paul M. West
(74) *Attorney, Agent, or Firm*—Merek, Blackmon & Voorhees, LLC

(57) ABSTRACT

A method for quantifying droplet fluxes of a water mist spray uses different measuring apparatuses and compares the measurements of the two apparatuses with one another. One of the measuring apparatuses is an iso-kinetic sampling probe in which the air velocity of the portion of the water spray mist entering the probe is made equal to the air velocity of the water mist spray around the probe by connecting a source of vacuum to the probe. The drops of the spray entering the probe are prevented from passing out of the probe. The air velocity of the spray entering the probe is measured by an anemometer, the drops of the entering spray are collected in a reservoir, and the depth of water in the reservoir is measured by a differential pressure transducer. The output of the pressure transducer is sent to a computer that calculates the water collection rate based on the sectional area of the probe opening and the water collection rate in the reservoir.

10 Claims, 2 Drawing Sheets

CHARACTERIZATION OF MIST SPRAYS USING A PHASE-DOPPLER PARTICLE ANALYZER AND AN ISO-KINETIC SAMPLING PROBE

CROSS-REFERENCE TO RELATED APPLICATION

This application claims the benefit of U.S. Provisional Application No. 60/528,483, filed Dec. 11, 2003, which is incorporated herein in its entirety by reference.

BACKGROUND OF THE INVENTION

The effectiveness of water mist fire protection systems for protection against industrial hazards has historically been evaluated by conducting full-scale fire tests in which a full size mock-up of a commodity is arranged as it would normally be found in industry. Although the fire protection industry still relies primarily on the full-scale fire testing approach to develop water mist fire protection systems, this approach drives up the cost and, thus, makes many potential applications economically prohibitive to develop. As a result, it is desirable to find a cost-effective testing method to evaluate the performance of water mist systems.

To replicate full-scale fire suppression phenomena with a geometrically similar scaled-down model, water mist sprays are used in a model simulation according to prescribed relationships with the scale ratio for drop size, total water mist discharge rate, mist flux and mist concentration. To ensure that appropriate water mist sprays that make the modeling valid are used, a two-dimensional Phase Doppler Particle Analyzer (PDPA) is used to screen candidate nozzles for use in the scaled-down model.

SUMMARY OF THE INVENTION

In accordance with the present invention, an iso-kinetic sampling probe (also called a "probe" herein) is used to independently measure water mist fluxes (also called "mist fluxes") at the same locations where PDPA measurements are made in order to ensure proper operation of the PDPA system in terms of optics selection, laser beam intensity, alignment, signal amplification and settings of droplet signal acceptance criteria. The probe includes a collection tube, a reservoir tube, internal flow obstructions to remove the drops from the sprays, a differential pressure measuring instrument, a settling chamber to dampen the pressure fluctuation in the reservoir tube, and a source of vacuum, such as a vacuum pump.

Collecting the mist flux at a location in the water mist spray is problematic because many of the drops are sufficiently small to follow the air currents of the spray. For example, simply placing a collection pan in the spray to measure the local mist flux will not collect a representative quantity of water because a portion of the mist will follow the air currents around and/or out of the pan. The probe mitigates this problem by introducing a vacuum to the collection tube such that the face velocity of air entering the collection tube equals the entrained air velocity in the water mist spray at that location. Several obstructions are included in the collection tube to force the coalescence of the drops, thereby preventing the drops from following the air currents through the tube and out the vacuum pump. A reservoir tube at the base of the collection tube collects the water, the depth of which is measured with a wet/wet differential pressure transducer. To mitigate the pressure fluctuation in the tube reservoir caused by the vacuum source, a settling chamber is provided upstream of the vacuum pump.

The probe provides accurate mist flux measurements of water mist sprays that cannot be done with conventional collection pans and cups. Features of the present invention include:

1) The face velocity of the probe is set equal to the mean air velocity of the spray at the measurement location. This allows collection of only those drops that, if the probe were absent, would have passed into the area that is now occupied by the collection area of the probe (i.e. the probe becomes 'invisible' in the spray). If the face velocity is set too high, then the probe will draw in drops from outside the collection area, and if the face velocity is set too low, many drops will not enter the probe due to air currents in the spray traveling around the collection area.

2) The internal structure of the probe forces the coalescence of the small drops, which allows for the drops to be collected in the reservoir tube. If the internal obstructions were not present, many of the drops would bypass the collection reservoir by following the air flow out through the source of vacuum.

3) The sampling probe can be scaled up or down to achieve desirable spatial resolution of measurements, depending on the lateral dimension of the water mist spray under consideration. The probe's capacity in terms of water mist collection rate can be increased or decreased by re-configuring the arrangement, including the size, of obstructions or baffles, and by adjusting the water passage openings inside the collection tube, the reservoir size, and the pressure drop between the probe opening and the source of vacuum. In this way, the probe can be adapted to different measuring conditions, including different liquids.

4) The wet/wet differential pressure transducer is used to measure the depth of water in the collection reservoir because a vacuum is applied to the probe. An absolute pressure transducer would not account for the effect of the vacuum on the water depth measurements and so would not accurately measure the water depth.

5) The collection tube is beveled at its opening to reduce the effect of wall thickness on the air currents around the probe opening.

6) The face velocity of the probe is measured with a hot-wire anemometer. Measurements are taken immediately above the probe opening at several locations around the perimeter.

The measurement accuracy of a PDPA is affected by optics selection, laser beam intensity, alignment, signal amplification and settings of droplet signal recognition criteria. Although a PDPA can be calibrated with individual water mist droplets with known diameters, its droplet identification capability is not as certain in a typical water mist spray due to: 1) multiple droplets being simultaneously present in the measuring volume, 2) droplets passing through the measuring volume in certain extreme angles relative to the PDPA's measuring volume, 3) the light intensity refracted from the same droplet depending on its location in the laser beam because the light intensity varies in the laser beam according to Gaussian distribution, etc. As a result, a PDPA may reject some legitimate data signals or accept some erroneous signals based on its signal acceptance criteria.

Although the method and apparatus of the present invention are described herein in connection with scale modeling of fire suppression systems, they can also be used in other scale modeling involving mist sprays, and for other purposes. Furthermore, they can be used with sprays of liquids other than water.

DETAILED DESCRIPTION OF THE PREFERRED EMBODIMENT

To ensure that appropriate water mist sprays that make modeling valid are used, a two-dimensional Phase Doppler Particle Analyzer (PDPA) is used to screen candidate nozzles for use in a scaled-down model. A traversing apparatus moves a candidate nozzle in a space, while the PDPA measuring volume is maintained stationary. Water is supplied to the nozzle from a tank pressured with nitrogen, air or other inert gas.

Figure 1:
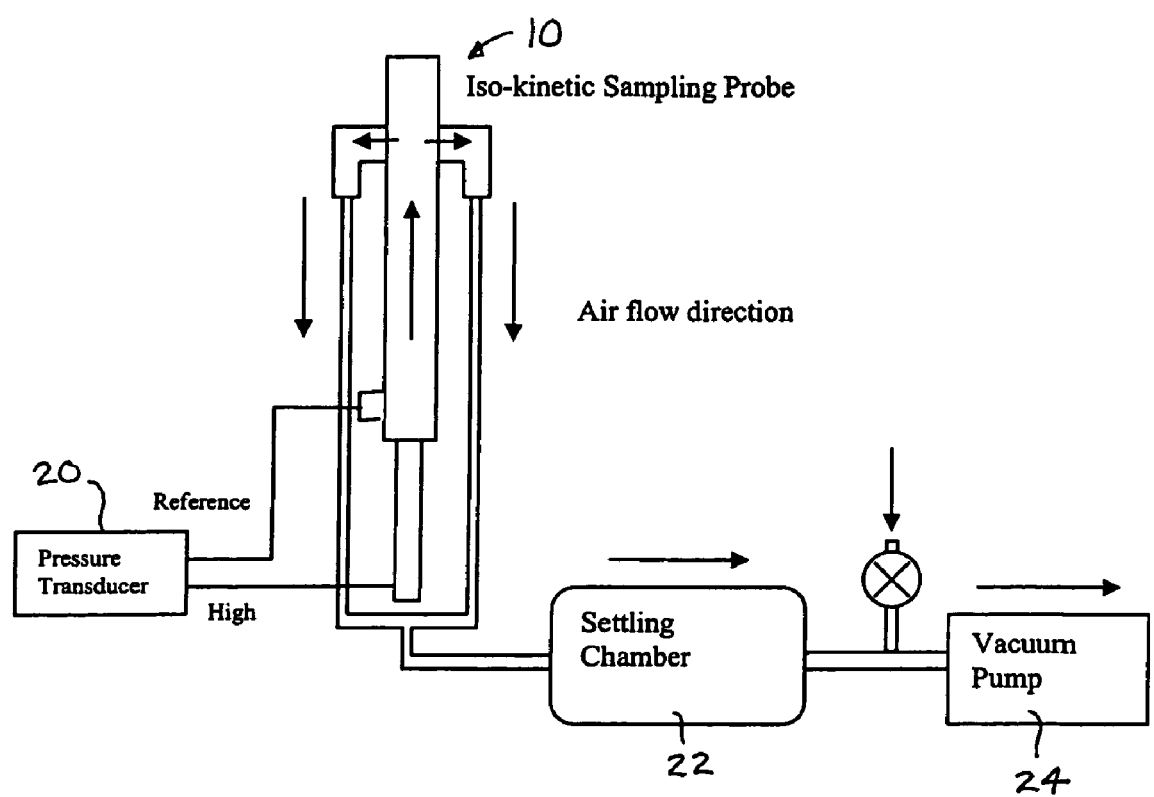
FIG. 1 is a schematic illustration of an iso-kinetic probe according to the present invention with associated apparatus.
Figure 2:
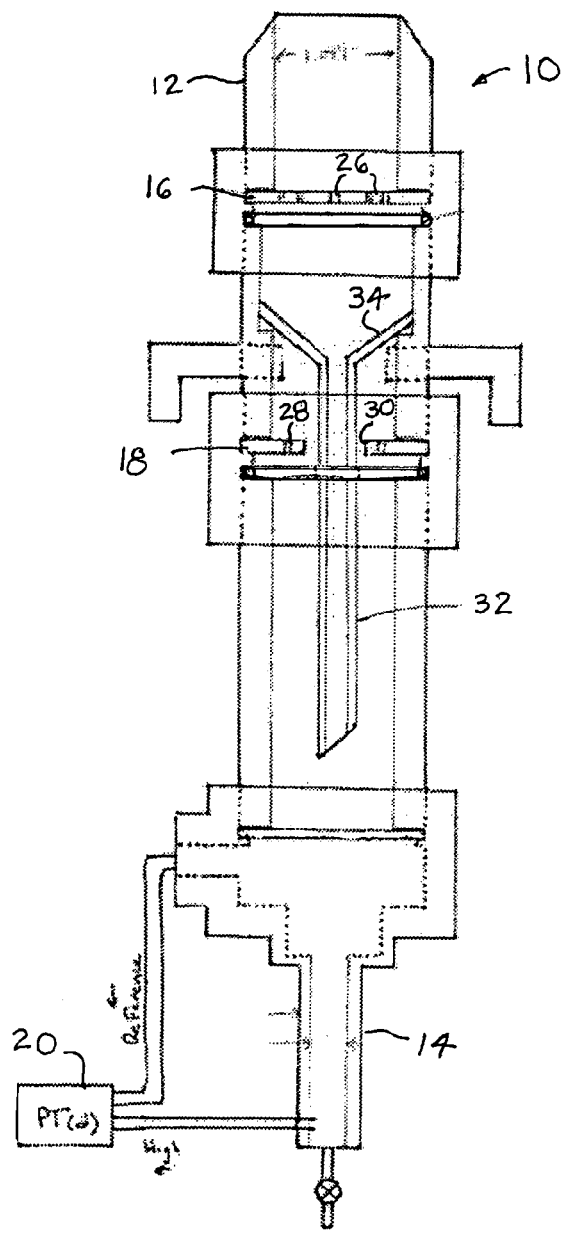
FIG. 2 is a vertical cross section through an iso-kinetic probe according to the present invention.
Figure 3:
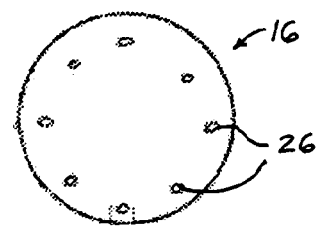
FIG. 3 is a plan view of a first orifice disc of the probe of FIG. 2.
Figure 4:
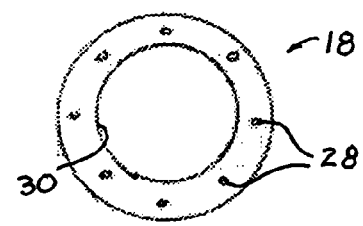
FIG. 4 is a plan view of a second orifice disc of the probe of FIG. 2.

In accordance with the present invention, an iso-kinetic sampling probe is used to independently measure water mist fluxes at the same locations where PDPA measurements are made. As can be seen from FIG. 2, a probe according to the present invention, which is designated generally by the numeral 10, includes a collection tube 12, a reservoir tube 14, and a series of internal baffles or obstructions 16 and 18. As can be appreciated from FIG. 1, also associated with the probe 10 are a differential pressure gauge 20, a settling chamber 22 to dampen pressure fluctuations in the reservoir tube 14, and a source of vacuum 24, such as a vacuum pump, which is connected to the probe by hoses. As can be seen in FIGS. 2–4, in the illustrated embodiment, the obstructions 16 and 18 are discs having small apertures 26 and 28, respectively. In addition, the obstruction 18 has a central opening 30 that receives the outlet tube 32 of a funnel 34 with a limited annular space between the outlet tube and the obstruction, so that drops cannot be carried between them by the flowing air. The water drops in the sprays that enter the collection tube 12 are separated from the air of the sprays when the air flows down through the apertures 26, turns upward after flowing through the funnel outlet tube 32, and flows up through the apertures 28. The size and arrangement of parts of the probe 10, such as the obstructions 16 and 18, the apertures 26 and 28, the central opening 30, the annular space between the funnel outlet tube 32 and the obstruction 18, can be adjusted to adapt the probe to different measuring conditions, including sprays of different liquids.

The vacuum source 24 imposes a vacuum on the collection tube 12 such that the face velocity of air entering the collection tube equals the entrained air velocity in the water mist spray at that location. The obstructions 16 and 18 are included in the collection tube 12 to force the coalescence of the drops, thereby preventing the drops from following the air currents through the tube and out to the source of vacuum 24. The reservoir tube 14 at the base of the collection tube 12 collects the water, the depth of which is measured with the differential pressure gauge 20, which is preferably a wet/wet differential pressure transducer connected to a data acquisition system, for example, a computer, or a meter or other indicator. To mitigate the pressure fluctuation in the tube reservoir 14 caused by the vacuum, the settling chamber 22 is provided upstream of the source of vacuum 24.

The 'high pressure' side of the differential pressure transducer 20 is connected just above the base of the collection reservoir 14, and the reference side of the transducer is connected to the collection tube 12 slightly above the collection reservoir. The transducer 20 is located horizontal to the 'high pressure' side connection, so that the measured pressure differential relates directly to the depth of water collected in the reservoir 14. The mist flux is then calculated based on the cross-sectional area of the opening of the collection tube 12 and the water collection rate in the reservoir 14.

The face velocity of the probe 10 is set equal to the mean air velocity of the spray at the measurement location. This allows collection of only those drops that would normally have passed into the area of collection tube 12 (i.e. the probe 10 becomes 'invisible' in the spray). If the face velocity is set too high, then the probe 10 will draw in drops from outside the collection area, and if the face velocity is set too low, many drops will not enter the probe due to air currents in the spray traveling around the collection area. The two velocities can be made equal by adjusting the vacuum imposed on the probe 10. One way of adjusting the vacuum is drawing in air through a valve 36 in fluid communication with the source of vacuum to partially reduce the vacuum imposed on the probe 10. Adjusting the valve adjusts the amount of vacuum. The adjustment can be made visually by observing the flow of the mist at and around the inlet to the probe. The adjustment can also be quantified with the PDPA while the water mist spray is present or with the hot wire anemometer while the spray is not present.

The internal structure of the probe 10 forces the coalescence of the small drops, which allows for the drops to be collected in the reservoir tube 14. If obstructions, such as the internal obstructions 16 and 18, were not present, many of the drops would bypass the collection reservoir 14 by following the air flow through the tube and out to the source of vacuum 24. The sampling probe 10 can be scaled up or down to achieve desirable spatial resolution of measurements, depending on the lateral dimension of the water mist spray. The probe's capacity in terms of water mist collection rate can be increased or decreased by re-configuring the arrangement of obstructions, and by adjusting: the water passage openings inside the collection tube 12, the size of the reservoir 14, and the pressure drop between the probe opening and the source of vacuum 24.

The transducer used to measure the depth of water in the collection reservoir 14 is a differential pressure transducer, because a vacuum is applied to the probe 10. An absolute pressure transducer would not account for the effect of the vacuum on the water depth measurements and so would not accurately measure the water depth. The collection tube 12 has a bevel surface facing radially outward at its opening to reduce the effect of wall thickness on the air currents around the probe opening. The face velocity of the air entering the probe 10 is measured with a hot-wire anemometer. Measurements are taken immediately above the probe 10 opening at several locations around its perimeter, and the output from the anemometer can go to a meter or a computer, such as a computer to which the output of the transducer 20 is connected.

With each candidate nozzle discharging vertically downward at an operating pressure, water fluxes are mapped out across a horizontal cross section of the spray. In general, the agreement between the mist fluxes as measured with the PDPA and as measured by the iso-kinetic sampling probe 10 improves with the Doppler signal quality of the PDPA.

The PDPA used for the modeling validation can include, for example, a 300 mW argon-ion laser, three sets of optics for the beam transmitter and receiver to cover drop sizes up to 2000 μm, and data processing electronics and software. A traversing apparatus moves candidate nozzles in a space measuring about 3.1 m×3.1 m×3.6 m high while the PDPA is maintained stationary. Water from a water tank pressurized with, for example, nitrogen gas is supplied to the nozzles through a high pressure rated flexible hose.

It will be apparent to those skilled in the art and it is contemplated that variations and/or changes in the embodiments illustrated and described herein may be made without departure from the present invention. Accordingly, it is intended that the foregoing description is illustrative only, not limiting, and that the true spirit and scope of the present invention will be determined by the appended claims.

The invention claimed is:

1. A method for quantifying mist fluxes in a liquid mist spray, comprising:

measuring the mist flux using a first measuring apparatus;

measuring the mist flux using an iso-kinetic sampling probe; and comparing the measurements of the first measuring apparatus and the iso-kinetic sampling probe with one another, wherein the liquid mist spray has an air velocity, the liquid mist spray enters the probe, and the step of measuring the mist flux using the iso-kinetic sampling probe comprises making the air velocity of the liquid mist spray entering the probe equal the air velocity of the liquid mist spray around the probe, wherein the step of measuring the mist flux using the iso-kinetic sampling probe comprises connecting the probe to a source of vacuum, and preventing the drops of the spray entering the probe from passing out of the probe, wherein the drops of the spray entering the tube are collected in a reservoir, and the depth of liquid in the reservoir is measured, and wherein pressure fluctuations in the reservoir are mitigated by a settling chamber between, and in fluid communication with, the reservoir and the source of vacuum.

2. The method of claim 1, wherein the first measuring apparatus is a Phase Doppler Particle Analyzer.

3. The method of claim 1, wherein the depth of liquid is measured by a wet/wet differential pressure transducer.

4. The method of claim 3, wherein the liquid mist spray enters the iso-kinetic sampling probe through an opening having a cross-sectional area, the wet/wet differential pressure transducer has an output that is sent to a computer that calculates the liquid collection rate in the reservoir, and the mist flux is calculated based on the cross-sectional area of the probe opening and the liquid collection rate in the reservoir.

5. The method of claim 1, wherein the liquid mist spray enters the probe through an opening defined by a tube having a bevel surface facing radially outward at the opening to reduce the effect of wall thickness on the air currents around the probe opening.

6. The method of claim 1, wherein the air velocity entering the probe is measured using a hot wire anemometer when the mist spray is absent.

7. A method for measuring mist fluxes of a liquid mist spray using an iso-kinetic sampling probe, wherein the liquid mist spray has an air velocity, comprising:

making a portion of the liquid spray mist enter an opening of the probe while another portion of the liquid spray mist flows around the probe such that the air velocity of the liquid mist spray entering the probe equals the air velocity of the liquid mist spray around the probe, wherein said air velocities are made equal by connecting the probe to a source of vacuum, wherein the drops of the spray entering the probe are prevented from passing out of the probe, wherein the drops of the spray entering the probe are collected in a reservoir, and the depth of liquid in the reservoir is measured, and wherein pressure fluctuations in the reservoir are mitigated by a settling chamber between, and in fluid communication with, the reservoir and the source of vacuum.

8. The method of claim 7, wherein the depth of liquid is measured by a wet/wet differential pressure transducer.

9. The method of claim 8, wherein the liquid mist spray enters the iso-kinetic sampling probe through an opening having a cross-sectional area, the wet/wet differential pressure transducer has an output that is sent to a computer that calculates the liquid collection cross-sectional area of the probe opening and the liquid collection rate in the reservoir.

10. The method of claim 7, wherein the liquid mist spray enters the probe through an opening defined by a tube having a bevel surface facing radially outward at the opening to reduce the effect of wall thickness on the air currents around the probe opening.

* * * * *